United States Patent [19]

Eichardt et al.

[11] Patent Number: 5,367,374
[45] Date of Patent: Nov. 22, 1994

[54] PLATFORM FOR A TRANSVERSELY-HEATED ELECTROTHERMAL ATOMIZER FURNACE FOR ATOM ABSORPTION SPECTROSCOPY

[75] Inventors: Klaus Eichardt, Jena, Germany; Bruno Hütsch, St. Vith,

[73] Assignee: Carl Zeiss Jena GmbH, Jena, Germany

[21] Appl. No.: 178,382

[22] Filed: Dec. 23, 1993

[30] Foreign Application Priority Data

Dec. 23, 1992 [DE] Germany ............ 4243767

[51] Int. Cl.$^5$ ............ G01N 21/74
[52] U.S. Cl. ............ 356/312; 356/244
[58] Field of Search ............ 356/312, 244

[56] References Cited

U.S. PATENT DOCUMENTS 4,407,582  10/1983  Woodriff ............ 356/312

FOREIGN PATENT DOCUMENTS

| 0381948 | 8/1990 | European Pat. Off. . |
| 2924123 | 12/1980 | Germany . |
| 3307251 | 9/1984 | Germany . |
| 221279 | 4/1985 | Germany . |
| 3545635 | 6/1987 | Germany . |
| 252249 | 12/1987 | Germany . |
| 8714670 | 2/1988 | Germany . |
| 3734001 | 4/1989 | Germany . |
| 3823346 | 1/1990 | Germany . |

OTHER PUBLICATIONS

"Improving the performance of the CRA atomizer by reducing the rate of diffusional atom loss and delaying analyte volatilization", Spectrochimica Acta, vol. 39B, Nos. 2/3, pp. 261 to 269 (1984).

*Primary Examiner*—F. L. Evans
*Attorney, Agent, or Firm*—Walter Ottesen

[57] ABSTRACT

The invention is directed to a platform for a transversely-heated electrothermal atomizer furnace which includes a furnace tube having a predetermined tube length and an inner wall surface defining an inner tube diameter. The platform includes first and second current-conducting holding rings provided in the furnace tube at first and second ends thereof, respectively, thereby narrowing the cross section of said furnace tube. The holding rings each have an outer diameter corresponding approximately to the inner tube diameter of the furnace tube and the rings taken together have a total thickness less than 40% of the tube length. A specimen carrier is fixedly connected to at least one of the holding rings and the specimen carrier and the one holding ring conjointly define an integral structural unit made of the same material. The specimen carrier is configured so as to be in spaced relationship to the inner wall surface of the furnace tube so that the specimen carrier has no electrical or direct thermal contact thereto.

26 Claims, 4 Drawing Sheets

FIG. 6.1
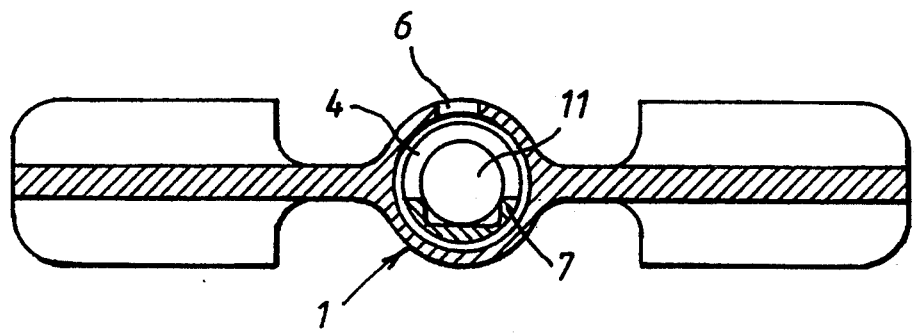
FIG. 6.2
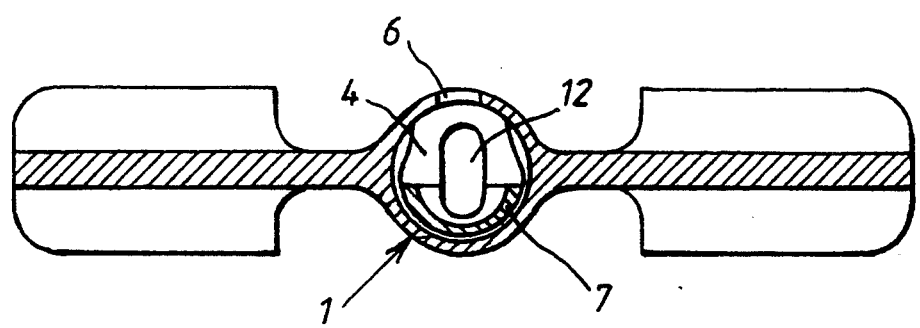
FIG. 6.3
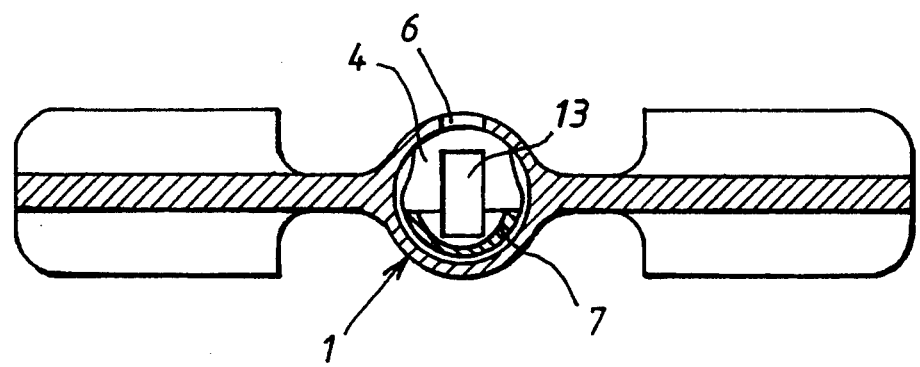

PLATFORM FOR A TRANSVERSELY-HEATED ELECTROTHERMAL ATOMIZER FURNACE FOR ATOM ABSORPTION SPECTROSCOPY

BACKGROUND OF THE INVENTION

In the area of electrothermal atomic absorption spectroscopy, electrically heated graphite furnaces are provided with tube-shaped longitudinally-heated furnace components. It is already known to provide so-called platforms in the interior of these tubes in order to delay the atomization of the specimen with respect to the electrothermal heating of the wall and of the interior of the furnace tube filled with protective gas.

These platforms are rectangular when viewed in plan and have a recess on their upper side for receiving a specimen. The platforms can be freely movable or can be fixed by direct body contact to the interior of the furnace tube or by struts formed thereon. In this connection, reference may be made to German patent publications 2,924,123; 3,545,635; 3,823,346; 3,734,001; and, DD 252,249.

The principle of the longitudinally-heated furnace tube has associated therewith the disadvantage of a temperature drop of several hundred degrees from the center of the tube to both tube ends. For this reason, the actually desired delay effect is overall reduced and limited only to a center region of constant tube temperature.

The platforms in the longitudinally-heated furnace tubes cannot be inserted and removed after each measuring operation for newly charging the same and for weighing the specimen without disturbing the entire system (the system comprising the tube and the current supply electrodes) in their existing electrical contact state. This, however, is necessary in the analysis of solid specimens.

European patent publication 0,381,948 discloses a transversely-heated furnace system wherein a platform of cylindrical shape is connected to the tube body via a strut in the vicinity of the center of the platform in order to generate the desired temperature-delay effect. Heat conduction from the wall of the tube to the platform takes place at the location of the strut which reduces the desired temperature-delay effect; that is, the temperature on the platform increases approximately as fast as the temperature of the tube wall and therefore more rapidly than the gas-phase temperature. Accordingly, the atomization of the specimen already begins before a thermal equilibrium is reached in the interior space of the tube.

A significant disadvantage of this configuration is furthermore that the spacing between the platform and the tube wall can change as a consequence of the necessary pressing pressure for the electrical contact.

This pressure acts on the surface of the tube body and because of this pressure, the tube body can be irreversibly deformed at the high temperatures which are applied which, in turn, leads to a direct contact to the platform.

In this case, the desired effect of the furnace system is cancelled.

U.S. Pat. No. 4,407,582 discloses the so-called tube-in-tube technology wherein the platform for the specimen has no direct thermal contact to the inner wall of the tube-shaped furnace body connected to the electrodes.

A conventional graphite tube is surrounded by an additional unstable heating jacket.

The impingement of radiation on the specimen is prevented by the interior tube.

The large mass to be heated and the necessary reduction of the overall diameter of the inner tube cause heat-up rates to be too long and introduce a limitation as to the area of application.

Possible unwanted transverse currents are facilitated.

The tube-in-tube technology is not utilized in commercial AAS-apparatus because of their disadvantages. Such a system is also disclosed in German patent publication 3,307,251.

German utility model registration 8,714,670 discloses a transversely-heated cuvette for use in atomic absorption spectroscopy. The cuvette has contact pieces formed laterally on the atomizer tube. A separate device for holding the specimen is not provided.

SUMMARY OF THE INVENTION

It is an object of the invention to provide a platform for a transversely-heated electrothermal atomizer furnace for atomic absorption spectroscopy which eliminates the above-described disadvantages and therefore improves the reliability of platform technology for transversely-heated furnace systems.

The invention provides a platform which can be inserted and removed and is not limited to liquid analysis and solid analysis. The configuration of the platform increases the service life of the tube-shaped furnace part and the analytic sensitivity and reproducibility of the overall furnace system.

The platform of the invention is for a transversely-heated electrothermal atomizer furnace which includes a furnace tube having a predetermined tube length and an inner wall surface defining an inner tube diameter. The platform includes: first and second current-conducting holding rings provided in the furnace tube at first and second ends thereof, respectively, thereby narrowing the cross section of the furnace tube; the holding rings each having an outer diameter corresponding approximately to the inner tube diameter and the rings taken together having a total thickness less than 40% of the tube length; a specimen carrier fixedly connected to at least one of the holding rings; the specimen carrier and the one holding ring conjointly defining an integral structural unit made of the same material; and, the specimen carrier being configured so as to be in spaced relationship to the inner wall surface so that the specimen carrier has no electrical or direct thermal contact thereto.

An automatic graphite furnace system for the solid analysis is provided by the insertability and removability of the platform in that the platform can be inserted and removed for charging and weighing of the specimen, for example, by a gripping system.

The ring-shaped holding parts are arranged at the ends of the specimen carrier and one of the ring-shaped parts and the specimen carrier conjointly define an integral uninterrupted unit made of the same material. Because of the ring-shape parts, a barrier is established at the ends of the tube which extends the residence time of the atoms in the tube and increases the density of the atom cloud. In this way, the problem described by Siemer et al in their article is approached and solved in a new and original manner. The article of Siemer et al is entitled: "Improving the performance of the CRA atomizer by reducing the rate of diffusional atom loss and delaying analyte volatilization" and is published in Spectrochimica Acta, Vol. 39B, no. 2/3, pages 261 to 269 (1984).

The above-mentioned holding rings are subjected to increased heating because of the current flowing therethrough. These holding rings reduce the otherwise usual losses as to analyte atoms occurring at the ends of the tube because of redepositing on these parts. The holding rings also reduce the temperature radiation and oppose the entry of cold protective gas from the outer furnace window areas.

The volume of the space in the tube wherein the generated atom cloud is present can be optimized by changes in the length of the specimen carrier.

The spatial and time-dependent heatup of the system can be influenced by means of the holding rings and therefore its sensitivity can be increased because current flows through the holding rings as a consequence of their contact to the tube wall. Accordingly, the position of the holding rings in the cuvette and their conductive cross section is of significance.

A plurality of influences on the spatial and time-dependent heating performance of the cuvette can be adjusted in the combination of the dimensioning of the holding rings with the construction of the current supply to the furnace tube.

A considerable strengthening of the resistance to pressure of the tube body is effected by the holding rings. In this way, a deformation because of the applied mechanical pressure for the electrical contact is thereby prevented.

An additional increase of the adherence between platform and tube is achieved by a pyrolytic coating in accordance with methods known from the technical literature after introducing the platform in the furnace tube. Accordingly, the specimen carrier cannot change its position.

The full intensity of the measuring radiation is significantly better utilized if the form of the inner recess of the holding rings is adapted to the profile of the measuring light beam of the generating light source in the specimen chamber of the spectrometer. The profile is different in dependence upon apparatus type. Accordingly, the detection capability and the reproducibility of each analysis are increased.

The platforms can, for example, comprise types of carbon such as graphite, pyrographite, pyrolytically-coated graphite and glass carbon or metallic materials (especially wolfram or tantal) or the platforms can be made of ceramic materials.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
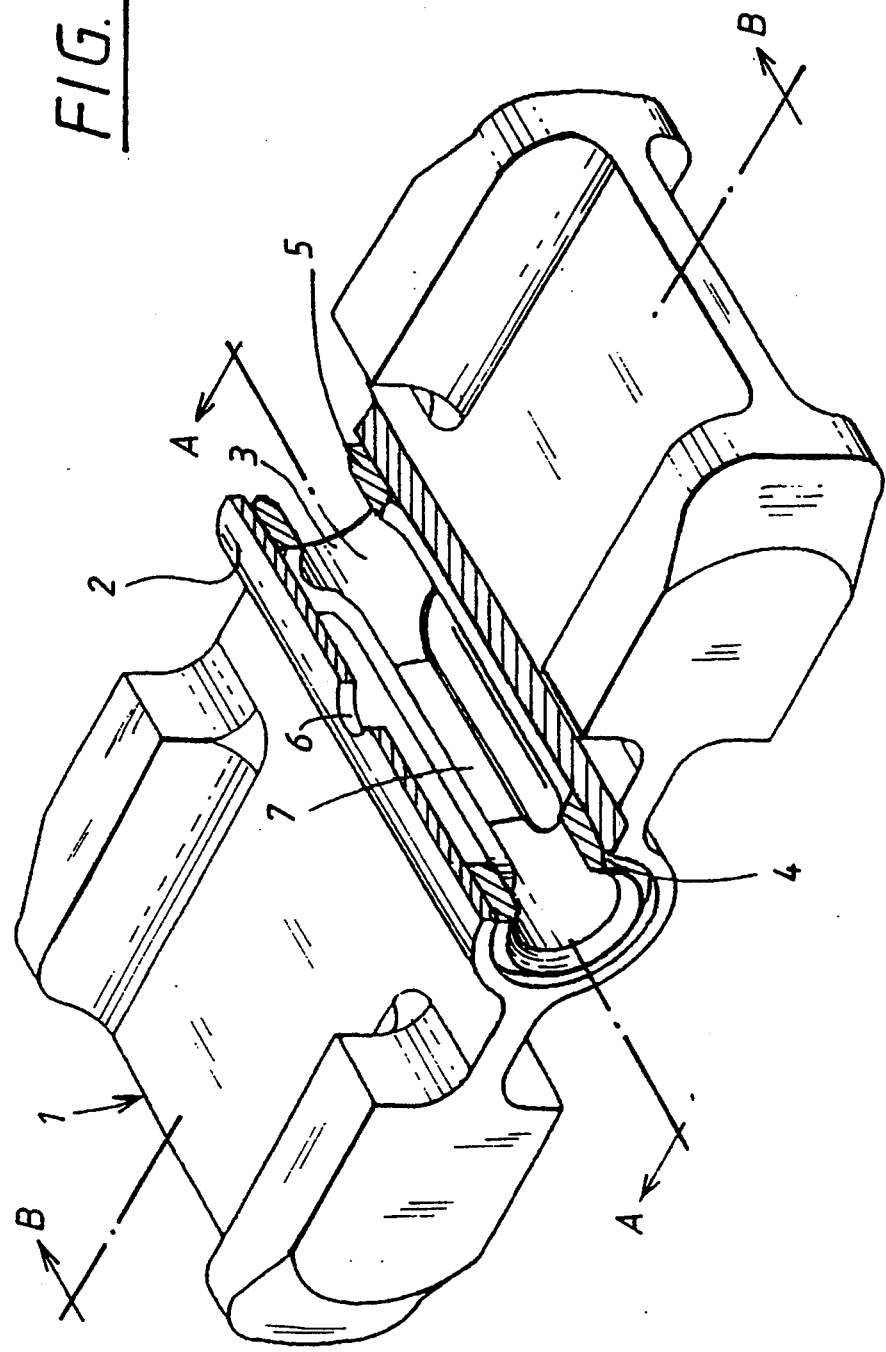
FIG. 1 is a perspective view of a furnace body wherein a portion of the furnace tube is broken away to show an embodiment of the platform according to the invention with holding rings at both ends of the specimen carrier.

A transversely-heatable furnace body 1 has a furnace tube 2 which holds a platform 3 which, in turn, includes two holding rings 4 and 5 which are electrically and mechanically ,connected to the furnace body via a pyrolytic coating. However, the platform 3 can also be inserted into the furnace body. The holding rings 4 and 5 are connected to a specimen carrier 7 via transition zones 6 shown in FIGS. 3 to 5.

The platform 3 is, in this way, only connected electrically and thermally to the furnace body 1 via the holding rings (4, 5). In combination with the transversely-heated embodiment of the furnace body 1, this leads to a situation where essentially no current flows through the specimen carrier 7 and therefore no joulean formation of heat takes place because the platform is only in contact engagement with zones of the same potential of the furnace tube 2 at rings 4 and 5.

Figure 3:
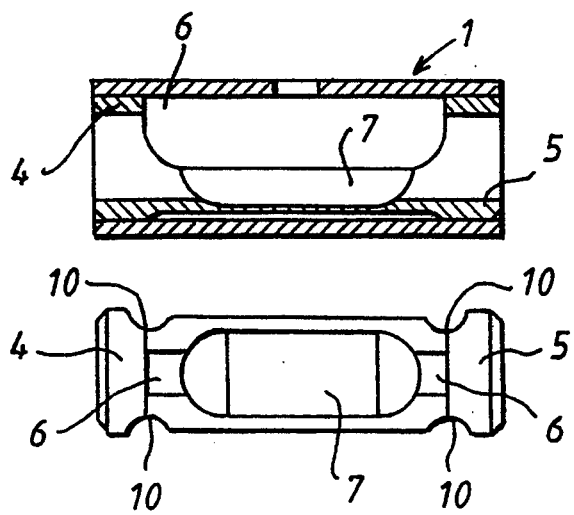
FIGS. 3, 4 and 5 show respective embodiments of a platform assembly of the invention with a section view taken through the longitudinal axis together with a plan view thereof; and, FIGS. 6.1 to 6.3 show three embodiments of the central opening of a holding ring with the view taken through the center of the furnace tube along line B—B of FIGS. 3 to 5, respectively.
Figure 4:
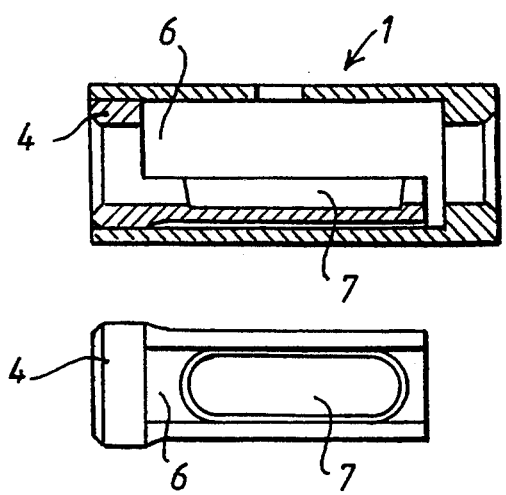
Figure 5:
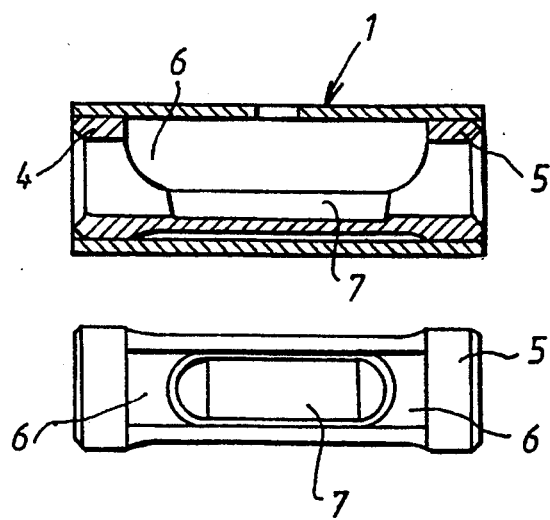

From FIGS. 3 to 5 it is apparent from the longitudinal sections that the specimen carrier 7 has no direct contact of any kind to the interior wall of the furnace tube 2.

The embodiment of FIG. 1 provides that the electrical and pyrolytic connection to the furnace tube 2 takes place at the rings 4 and 5. This embodiment is especially suitable for liquid specimen forms because the specimen carrier cannot be changed with respect to its position which leads to measurements of excellent reproducibility.

Figure 2:
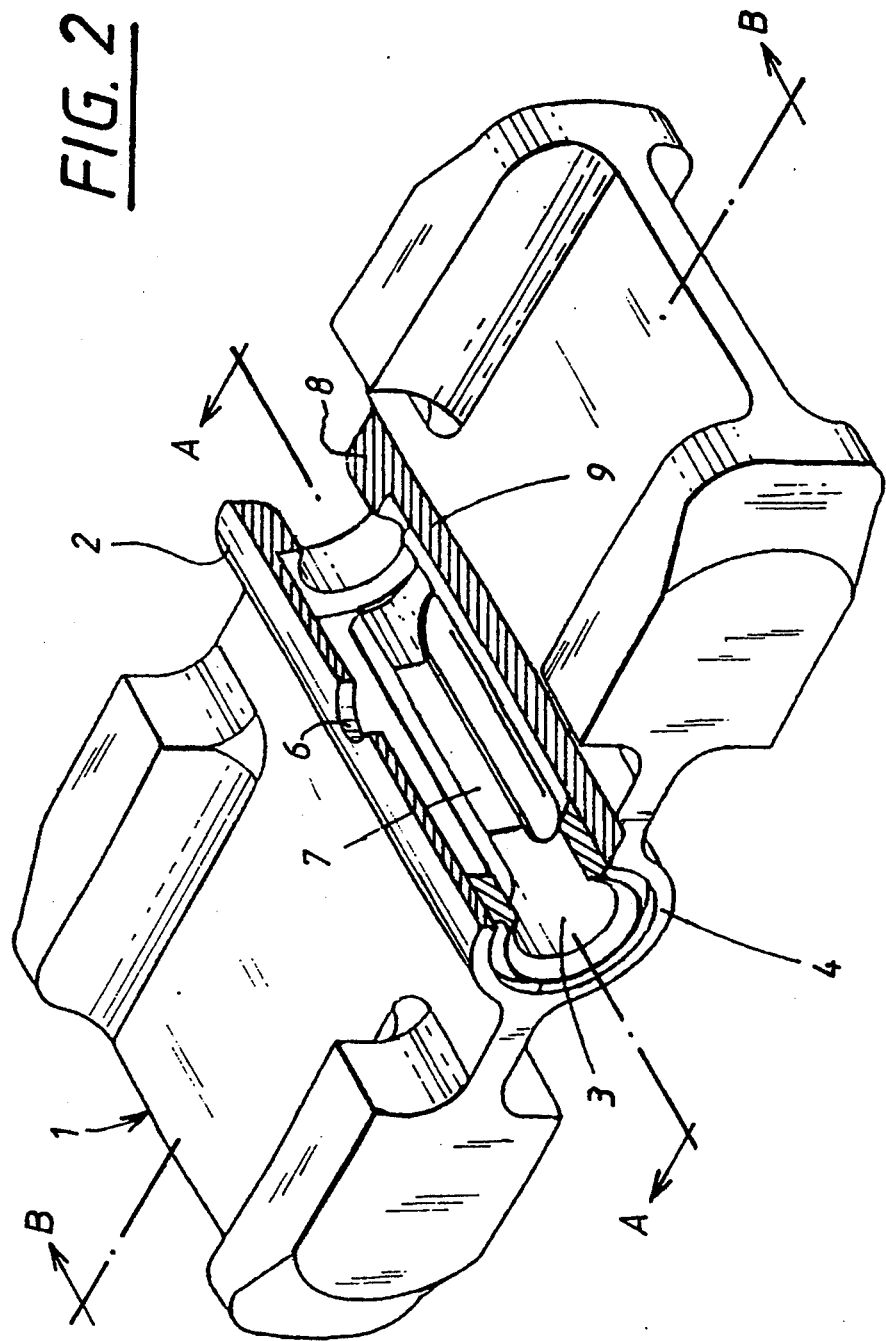
FIG. 2 is a perspective view similar to that in FIG. 1 but wherein the platform assembly includes only one holding ring while a second holding ring is formed in the interior of the furnace tube.

In FIG. 2, and as shown in FIG. 5, the platform 3 comprises only one holding ring 4 as well as the specimen carrier 7 formed thereon via the transition zone 6.

A holding ring 8 is formed onto the end of the tube 2 lying opposite the holding ring 4 in the tube interior. The holding ring 8 has the same geometry as the holding ring 4. A gap 9 is thereby formed between the specimen carrier 7 and the holding ring 8. This gap 9 prevents a direct current flow through the specimen carrier 7 of the platform 3.

The holding ring 8 can be produced either directly by boring out the tube 2 and leaving a thickening or the holding ring 8 can be provided subsequently as a separate individual piece in advance of the pyrolytic coating process and thereby be pyrolytically connected to the furnace tube.

The embodiment of FIG. 2 is especially suitable (as is also the embodiment of FIG. 1) for a solid specimen which is disposed on the specimen carrier 7 and can be introduced together with the platform 3 into the tube interior. For this purpose, generally known guidance means (not shown) such as a lug engaging into a slot can be provided at the interface of the platform and the tube in order to position the platform in the interior of the tube.

In FIG. 3, the transition zones 6 advantageously include constrictions 10 for influencing (delaying) the conduction of heat from the holding rings to the specimen carrier. The specimen carrier 7 includes a trough-shaped recess for receiving the specimen and this recess prevents the specimen liquid from escaping from the recess in the direction of the ends of the tube body or in the direction of the interior surface of the tube body. This is especially the case during the drying operation.

In FIG. 4, a tub-shaped recess for receiving the specimen is provided which is especially simple to produce. This recess can, for example, be produced by machining with a straight-shank cutter in the embodiment where the platform 3 has only one holding ring 4.

FIG. 5 shows the embodiment of FIG. 4 but with two holding rings 4.

FIGS. 6.1 to 6.3 show respective geometric configurations (11, 12, 13) of the central openings of the carrier rings 4, 5 or 8. These openings are adapted to the particular form of the measuring light beam of the spectrometer, that is, a round cross section in FIG. 6.1, an oval cross section or elipsoidal cross section in FIG. 6.2 and a rectangular cross section in FIG. 6.3.

The forms of the central openings (11, 12, 13) as well as their dimensions can be furthermore varied in other directions.

The residence time and the atom density of the analyte atoms in the tube interior during the atomizing steps of an analysis program can be increased by reducing the dimensions of the recess. This can be achieved without disturbing the advance steps of drying and thermal preprocessing of the specimen in their operation and coaction with the internal protective gas flows.

It is understood that the foregoing description is that of the preferred embodiments of the invention and that various changes and modifications may be made thereto without departing from the spirit and scope of the invention as defined in the appended claims.

What is claimed is:

1. A platform for a transversely-heated electrothermal atomizer furnace which includes a furnace tube having a predetermined tube length and an inner wall surface defining an inner tube diameter, the platform comprising:
   first and second current-conducting holding rings provided in said furnace tube at first and second ends thereof, respectively, thereby narrowing the cross section of said furnace tube;
   said holding rings each having an outer diameter corresponding approximately to said inner tube diameter and said rings taken together having a total thickness less then 40% of said tube length;
   a specimen carrier fixedly connected to at least one of said holding rings;
   said specimen carrier and said one holding ring conjointly defining an integral structural unit made of the same material; and,
   said specimen carrier being configured so as to be in spaced relationship to said inner wall surface so that said specimen carrier has no electrical or direct thermal contact thereto.

2. The platform of claim 1, further comprising transition zone means connecting said specimen carrier to at least one of said holding rings for controlling the flow of heat.

3. The platform of claim 1, wherein at least one of said holding rings is fixedly connected to said furnace tube by a pyrolytically applied layer.

4. The platform of claim 1, wherein said specimen carrier is fixedly connected to both of said holding rings and said holding rings and said specimen carrier conjointly define an integral structural unit made of the same material.

5. The platform of claim 1, wherein said platform is removable and replaceable in said furnace tube as a separate unit.

6. The platform of claim 5, wherein the other one of said holding rings is formed on said furnace tube so as to extend inwardly from said inner wall surface and so as to be integral with said furnace tube; and, said other one of said holding rings having the same geometric configuration as said one holding ring.

7. The platform of claim 6, said specimen carrier and said other one of said holding rings conjointly defining a gap therebetween.

8. The platform of claim 5, both of said holding rings being fixedly connected to said specimen carrier.

9. The platform of claim 1, said furnace tube defining an optical axis and said holding rings defining respective central openings on said axis; and, said openings having a form adapted to a measuring light beam.

10. The platform of claim 9, said form of said openings being a circular shape.

11. The platform of claim 9, said form of said openings being a vertical gap.

12. The platform of claim 9, said form of said openings being oval.

13. The platform of claim 11, said vertical gap being rectangular.

14. The platform of claim 11, said vertical gap being ellipsoidal.

15. The platform of claim 1, said specimen carrier defining a trough-shaped recess.

16. The platform of claim 1, said specimen carrier defining a tub-shaped recess.

17. The platform of claim 1, further comprising guide means for guiding said platform into said furnace tube.

18. The platform of claim 2, said transition zone means including constrictions and/or breakthroughs for influencing the flow of heat from said one holding ring to said specimen carrier.

19. The platform of claim 1, wherein said platform is made of graphite or pyrolytically coated graphite.

20. The platform of claim 1, wherein said platform is made of a ceramic material.

21. The platform of claim 1, wherein said platform is made of glassy carbon.

22. The platform of claim 1, wherein said platform is made of a metal material.

23. The platform of claim 1, wherein said platform is made of wolfram.

24. The platform of claim 1, wherein said platform is made of tantal.

25. The platform of claim 1, wherein said platform is made of pyrographite.

26. The platform of claim 9, said central opening being reduced by a minimum required for the detection capacity and for the reproducibility of the analysis.

* * * * *